United States Patent [19]

Chiesi et al.

[11] Patent Number: 6,034,277

[45] Date of Patent: Mar. 7, 2000

[54] PROCESS FOR THE PREPARATION OF 5,6-DIHYDROXY-2-AMINO-1,2,3,4-TETRAHYDRONAPHTHALENE DERIVATIVES

[75] Inventors: Paolo Chiesi; Paolo Ventura; Vittorino Servadio; Maurizio Del Canale; Renato De Fanti; Gabriele Amari, all of Parma, Italy

[73] Assignee: Chiesi Farmaceutici S.p.A., Parma, Italy

[21] Appl. No.: 09/325,350

[22] Filed: Jun. 4, 1999

Related U.S. Application Data

[62] Division of application No. 08/962,706, Nov. 3, 1997, Pat. No. 5,936,125, which is a division of application No. 08/722,227, filed as application No. PCT/EP95/01406, Apr. 13, 1995, Pat. No. 5,710,336.

[30] Foreign Application Priority Data

Apr. 26, 1994 [IT] Italy .................................. MI94A0802

[51] Int. Cl.⁷ .................................................. C07C 211/38
[52] U.S. Cl. ............................................................. 564/428
[58] Field of Search ............................................. 564/428

[56] References Cited

U.S. PATENT DOCUMENTS

5,221,770 6/1993 Bertolini et al. ......................... 564/428

*Primary Examiner*—Mukund J. Shah
*Assistant Examiner*—Tamthom N. Truong
*Attorney, Agent, or Firm*—Oblon, Spivak, McClelland, Maier & Neustadt, P.C.

[57] ABSTRACT

A process, and variations thereof, for the preparation of 5,6-dihydroxy-2-amino-1,2,3,4-tetrahydronaphthalene derivatives of formula (I), wherein $R_1$, $R_2$, $R_3$ can independently be hydrogen or lower alkyl.

4 Claims, No Drawings

PROCESS FOR THE PREPARATION OF 5,6-DIHYDROXY-2-AMINO-1,2,3,4-TETRAHYDRONAPHTHALENE DERIVATIVES

This application is a Division of application Ser. No. 08/962,706 filed on Nov. 3, 1997, now U.S. Pat. No. 5,936,125, which is a divisional application of application Ser. No. 08/722,227, which was filed as international application PCT/EP95/01406, filed Apr. 13, 1995, now U.S. Pat. No. 5,710,336.

The present invention relates to a process for the preparation of 5,6-dihydroxy-2-amino-1,2,3,4-tetrahydronaphthalene (or aminotetralin) (5,6-ADTN) derivatives of formula (I):

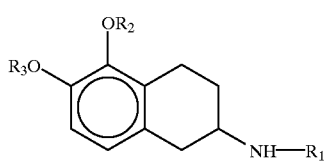

wherein $R_1$, $R_2$ and $R_3$, which are the same or different, are hydrogen or a straight or branched lower alkyl group.

TECHNICAL BACKGROUND

Aminotetralins are compounds having remarkable sympathomimetic activity.

Thanks to their properties, they can be used in different therapeutical fields as medicaments active at the bronchial, cardiovascular, renal and central nervous system levels.

A number of methods for the preparation of 5,6-ADTN are described in literature or in patents starting from the end of the 60s.

Some syntheses require the preparation of 5,6-dimethoxy-1-tetralone which is then transformed into 5,6-ADTN by means of various procedures: by Neber rearrangement of 5,6-dimethoxy-1-tetralone O-tosyl oxime (W. K. Sprenger et al., J. Med. Chem., 12, 487, 1969 modified by J. C. Kim et al., J. Kor. Chem. Soc., 21(3), 187, 1977), by α-bromination and subsequent substitution of bromine (J. C. Kim et al., J. Kor. Chem. Soc., 20, 91, 1976; Y. Oka et al., Chem. Pharm. Bull., 25(4), 632, 1977), by α-nitrosation and subsequent reduction (Y. Oka et al., Chem. Pharm. Bull., 25(4), 632, 1977).

Some syntheses require the preparation of 5,6-dimethoxy-2-tetralone which is then transformed into the corresponding 2-amino derivative by reductive amination (J. D. McDermed et al., J. Med. Chem., 18(4), 362, 1975; J. G. Cannon et al., J. Med. Chem., 20(9), 1111, 1977; U.S. Pat. No. 646,300, 1976 (Iowa Univ.) or by transformation into the corresponding O-methyloxime and subsequent reduction (J. G. Cannon et al., J. Med. Chem., 17(5), 565, 1974).

Some syntheses are based on the preparation of 5-hydroxy-6-methoxy-1,2,3,4-tetrahydro-2-naphthoic acid and the subsequent transformation into 5,6-ADTN by Curtius rearrangement (K. Mitsuhashi et al., Chem. Pharm. Bull., 20(6), 1321, 1972).

The only enantiospecific synthesis of 5,6-ADTN is based on the use of 2,2-dimethyl-3-methoxycarbonyloxazolidine-4-aldehyde (A. D. Baxter et al., Tetrahedron Letters, 33(17), 2331, 1992).

All these methods suffer from severe restrictions for the industrial use.

Recently, a method for the preparation of 2-amino-5,6-dimethoxytetralin applicable industrially has been claimed in EP-A-0 534 536, filed on Sep. 17, 1991, in Zambon's name.

According to the latter reference, 5,6-dimethoxy-2-aminotetralin is obtained through the key intermediate, i.e. the corresponding 1-tetralone, already widely described in the literature cited above. The tetralone is obtained starting from condensation of 2,3-dimethoxybenzaldehyde with pyruvic acid (step A), transformation of the keto group into amino group and reduction of the unsaturated amino acid (step B) and intramolecular cyclization to give the desired 5,6-dimethoxy-2-amino(protected)-1-tetralone.

The condensation reaction (A) had already been described by Hudson et al., J. Chem. Soc., 715–722 (1941) and Pavel et al., Acta Univ. Palacki Olomuc. Fac. Rerum. Natur., 401–404 (1971).

On the subject, EP 0 534 536 stresses that such a reaction was carried out in the presence of an inorganic base, such as sodium hydroxide (Hudson) or potassium carbonate (Pavel) with very low yields (respectively 40 and 6%), and therefore it showed no industrial interest.

In EP 0 534 536 cited above, the problem of the low yield is overcome by carrying out the condensation in the presence of an organic base, such as triethylamine, piperidine, piperazine and morpholine. The condensation product is obtained in yields up to about 80%. The condensation described therein requires particular reaction conditions, such as an anhydrous organic solvent (dimethylformamide is cited), inert atmosphere, low temperatures during the reagent addition phase. The recovery of the product requires an extraction procedure to remove the organic solvent.

From the industrial point of view, the condensation described above has additional costs in terms of reagents, anhydrous solvents and plant requirements.

Now it has been found that the condensation reaction of 2,3-dialkoxybenzaldehyde and pyruvic acid allows to obtain 4-(2,3-dialkoxyphenyl)-2-ketobutenoic acid in high yields, when carried out in the presence of an inorganic base in an aqueous/alcoholic solvent. The reaction is carried out at room temperature.

SUMMARY OF THE INVENTION

It is an object of the present invention a process for the preparation of compounds of formula (I)

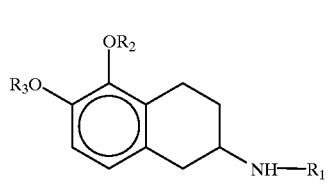

which comprises:
a) condensation of 2,3-dialkoxybenzaldehyde with pyruvic acid in an aqueous/alcoholic system and in the presence of an inorganic base, to obtain 2-keto-4-(2,3-dialkoxyphenyl)-butenoic acid;
b) transformation of the keto group of said acid into an amino or alkylamino group with simultaneous reduction of the double bond, to give respectively 2-amino or 2-alkylamino-4-(2,3-dialkoxyphenyl)butyric acids;
c) transformation of 2-amino or 2-alkylamino-4-(2,3-dialkoxyphenyl) butyric acid into 4-(2-( 2,3-dialkoxyphenyl)ethyl)-N-alkyl-2,5-oxazolidinedione;

d) cyclization of the N-carboxyanhydride by Friedel-Crafts intramolecular acylation in the presence of a Lewis acid, to give directly the non protected 5,6-dialkoxy-2-alkylamino-1-tetralone;

e) catalytic reduction of the ketone to give 5,6-dialkoxy-2-alkylaminotetralin and, if desired, f) O-dealkylation of 5,6-dialkoxy-2-alkylaminotetralin to give 5,6-dihydroxy-2-alkylaminotetralin.

The process can be shortened using an halohydric acid or a Lewis acid under suitable conditions, to obtain directly the unprotected 5,6-dihydroxy-2-alkylamino-1-tetralone from N-carboxyanhydride.

In another aspect, the process of the present invention comprises the steps a) and b) described above, then:

c) cyclization of 2-alkylamino-4-(2,3-dialkoxyphenyl) butyric acid with simultaneous dealkylation on the oxygen, to give the 2-alkylamino-5,6-dihydroxy-1-tetralone directly in a single step;

d) catalytic reduction of the ketone to give 5,6-dihydroxy-2-alkylaminotetralin hydrochloride.

The final compound is usually obtained in form of a salt, but the process according to the present invention also provides the transformation of the derivative into the free base or the conversion thereof into another acid addition salt.

Examples of lower alkyl group are straight or branched $C_1$–$C_4$ alkyl groups.

In a preferred embodiment, the present invention provides a process for the preparation of compounds of formula (I) wherein $R_1$ is methyl and $R_2$ and $R_3$ are H.

DETAILED DISCLOSURE OF THE INVENTION

According to a first embodiment of the present invention, the compounds of formula (I) are prepared according to the following scheme 1:

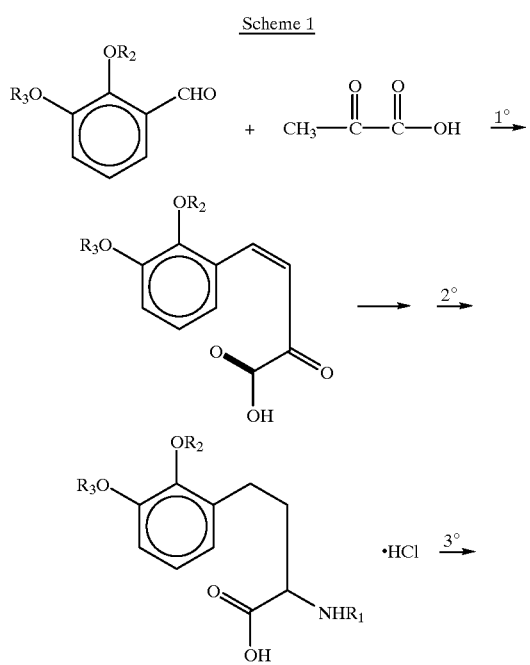

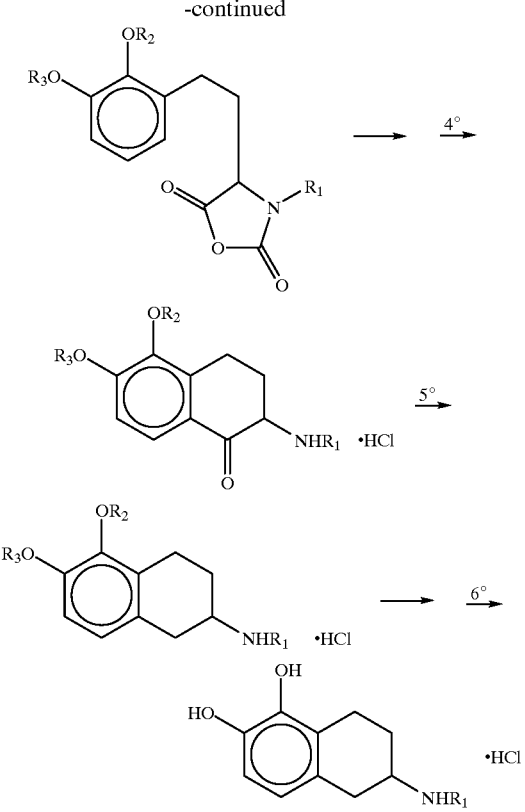

In the following, the single steps are described in detail:

1st step

The condensation reaction of 2,3-dimethoxybenzaldehyde with pyruvic acid is already known by literature, as mentioned above.

According to the present invention, the reaction can be carried out in 80% yields, operating in an aqueous/alcoholic medium, preferably water/ethanol and using an inorganic base, preferably commercial potassium hydroxide.

Other inorganic bases which can be employed according to the present invention are, for example, sodium hydroxide.

2nd step

It consists in the transformation of the ketone into an alkylamino group by reductive amination. The transformation is carried out in a single step with conventional procedures, using a suitable alkylamine, for example aqueous methylamine, and a suitable reducing system, for example by catalytic hydrogenation (catalyst Pd) in methanol. The reaction takes place with simultaneous reduction of the double bond in a single step in about 60% yields. The reaction is carried out using methylamine or other alkylamines, thus allowing to obtain directly 2-aminotetralin derivatives already substituted on the amino group with alkyl groups, which in their turn are optionally substituted. The medium is an alcoholic or hydroalcoholic solution, under easy and cost-saving conditions.

The amino acid can be obtained both in form of the hydrochloride and the neutral amino acid (ampho-ion).

The method can be carried out using ammonia instead of alkylamine, to also obtain 2-aminotetralin derivatives non substituted on the amine.

3rd step

The transformation of the amino acid into the corresponding cyclic N-carboxyanhydride takes place in a single step using phosgene, according to conventional methods (cfr. A. R. Katritzky, C. W. Rees Comprehensive Heterocyclic Chemistry, part 4B, page 231, 1984, Pergamon Press; J. P. Greenstein, M. Winitz Chemistry of the Amino Acids, vol. 2, pages 867–868, 1961 and ref. cit.).

For practical purposes, it is preferred to subdivide the reaction into two steps:

transformation of the amino group of 2-alkylamino-4-(2, 3-dialkoxyphenyl)butyric acid into carbamate, using a suitable chloroformate, for example benzyl chloroformate or ethyl chloroformate, in a quantitative yield;

cyclization of 4-(2,3-dialkoxyphenyl)-2-(N-alkyl-N-alkyloxycarbonylamino)butyric acid to cyclic N-carboxyanhydride with simultaneous elimination of alkyl halide, for example by means thionyl chloride, in the absence or in the presence of an organic solvent. Yields are nearly quantitative.

The resulting product is solid, stable and easy to handle without specific operative attentions. As far as we know, the use of this particular anhydride in the preparation of compounds with an aminotetralin structure has never been described in literature.

This method allows to obtain directly the 2-alkylamino-5,6-dialkoxy-1-tetralone in the subsequent step, avoiding the amino group protection/deprotection procedure, which on the contrary is required in EPO 0 534 536.

4th step

This step consists in a Friedel-Crafts intramolecular acylation of 4-(2-(2,3-dialkoxyphenyl)ethyl)-N-alkyl-2,5-oxazolidinedione to give 5,6-dialkoxy-2-alkylamino-1-tetralone, carried out with conventional procedures, using for example aluminium trichloride or other suitable Lewis acids (such as $BBr_3$, $BCl_3$, $SnCl_4$, $TiCl_4$) in an anhydrous aprotic solvent, preferably chlorinated.

5th step

The reduction of 5,6-dialkoxy-2-alkylamino-1-tetralone to tetralin is carried out in aqueous or hydroalcoholic medium, acid by hydrochloric acid, using Pd on carbon as catalyst. Yields are nearly quantitative.

6th step

The possible O-dealkylation reaction of 5,6-dialkoxy-2-alkylaminotetralin to give 5,6-dihydroxy-2-alkylaminotetralin is carried out with conventional procedures, for example using a suitable concentrated halohydric acid (such as aqueous HBr) or a suitable Lewis acid in aprotic apolar solvent (for example aluminium trichloride in anhydrous toluene), in nearly quantitative yields.

In a second embodiment of the present invention, compounds of formula (I) are prepared according to the following scheme 2:

Scheme 2

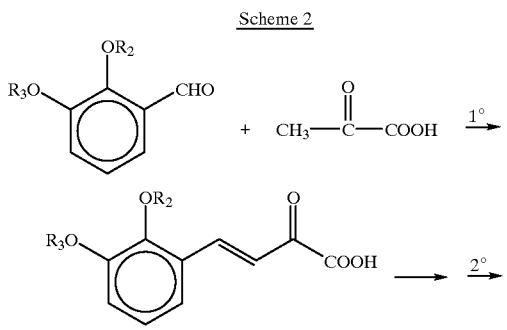

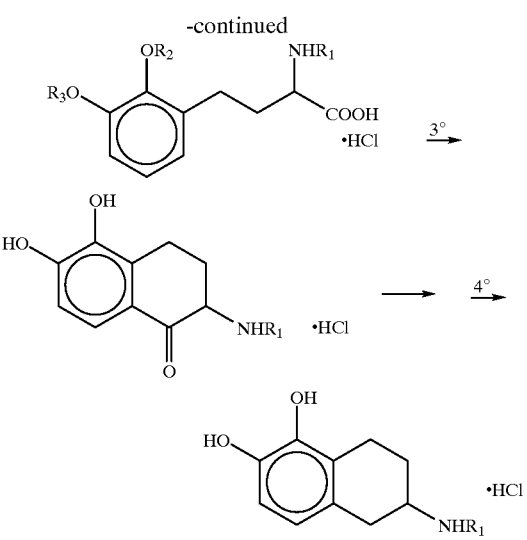

The single steps are described in detail in the following:

Process 2

1st step and 2nd step

They are carried out according to the procedures described for steps 1 and 2 of Process 1.

3rd step

This step consists in the cyclization by intramolecular acylation of the amino acid with simultaneous deprotection of the catechol hydroxyls. The reaction takes place using a suitable aqueous concentrated halohydric acid, for example 48% hydrobromic acid under reflux, 37% hydrochloric acid at a temperature from 100 to 140° C. under pressure or 57% hydroiodic acid. The reaction can also be carried out using a suitable Lewis acid in aprotic solvent (for example $BBr_3$ in methylene chloride). This step is particularly important.

In fact, as far as the Applicant knows, no methods described in literature achieve in a single step the intramolecular cyclization with the simultaneous deprotection of the hydroxyls, avoiding the protection and deprotection steps of the amino or alkylamino group.

In fact, the usually described methods involve a) the protection of the amino group and the cyclization according to Friedel-Crafts or in a single-step with trifluoroacetic anhydride in trifluoroacetic acid (see EP 0 534 536) or in more steps (see literature cited in EPO 0 534 536 and A. D. Baxter et al. Tetrahedron Letters, 33(17), 2331, 1992); b) the deprotection of the amino group; c) the deprotection of the hydroxyls, generally be treatment with hydrobromic acid; d) the possible N-alkylation of the 2-aminotetralin.

Moreover, the present method is particularly interesting industrially due to the high yields (about 90%) and the low costs of the reagents.

When using an acid different from the hydrochloric one, the product is transformed into the hydrochloride simply by treatment with concentrated hydrochloric acid, to obtain the desired salification quantitatively.

The process can also be used starting from an amino acid in the optically active form, to obtain the corresponding enantiomer of 2-(alkyl)amino- 5,6-dihydroxy-1-tetralone.

4th step

This step consists in the reduction of 2-alkylamino-5,6-dihydroxy-1-tetralone to give 2-alkylamino-5,6-dihydroxytetralin by catalytic hydrogenation. The reaction is carried out in aqueous or hydroalcoholic medium, acid by hydrochloric acid, using Pd on carbon as the catalyst. Yields are nearly quantitative.

According to the process of the present invention, including the above described modification thereof, 5,6-dihydroxy-2-aminotetralin derivatives substituted at the amine with an alkyl group are obtained directly, which group in its turn can optionally be substituted.

In a first embodiment, the process provides the use of N-carboxy-anhydride, having the double function of protecting the amine and activating the carboxyl, and from which 5,6-dimethoxy or 5,6-dihydroxy-2-methylamino-1-tetralone is obtained by subsequent cyclization, avoiding the amine deprotection step.

The second embodiment of the process of the present invention is even more advantageous since it allows to obtain 5,6-dihydroxy-2-alkylaminotetralin starting from 2-alkylamino-4-(2,3-dialkoxyphenyl)butyric acid in two only steps, of which one is the cyclization and simultaneous dealkylation of the catechol group and the other is the reduction.

As far as we known, this is the simplest and most direct method to obtain 5,6-dihydroxy-2-(alkyl)aminotetralin and in particular 5,6-dihydroxy-2-methylaminotetralin.

According to a third embodiment of the invention, compounds of formula (I) are prepared according to the following scheme 3:

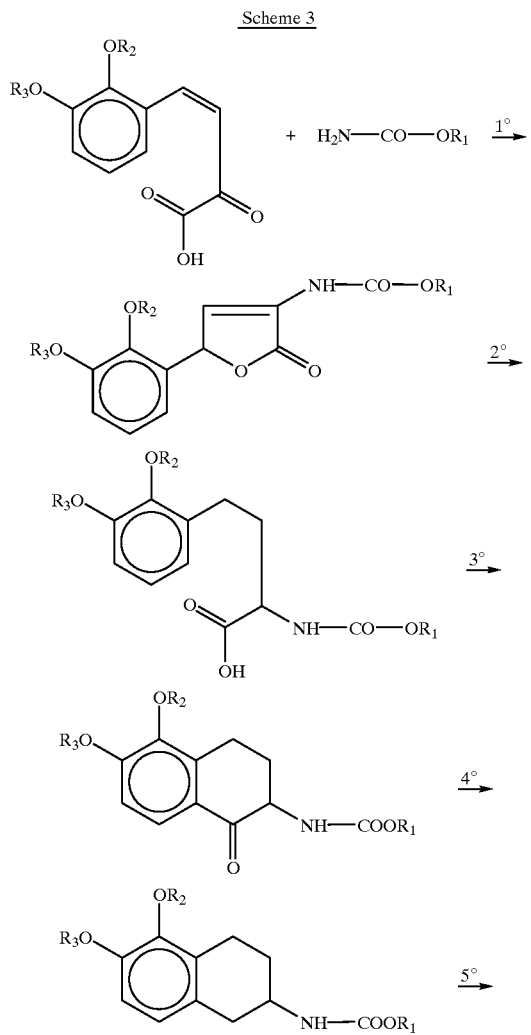

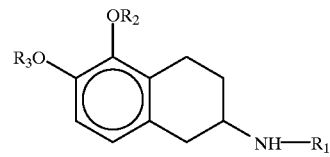

in which $R_1$ is methyl.

Such a process comprises:
a) condensation of 4-(2,3-dialkoxyphenyl)-2-ketobutenoic acid with a lower alkyl carbamate to give 5-(2,3-dialkoxyphenyl)-3-alkoxycarbonylamino-2,5-dihydrofuran-2-one;
b) reduction of the condensation product to give 4-(2,3-dialkoxyphenyl)-2-alkoxycarbonylaminobutyric acid;
c) intramolecular cyclization to give 5,6-dialkoxy-2-alkoxycarbonylamino-1-tetralone;
d) reduction of the keto group to give 5,6-dialkoxy-2-alkoxycarbonylaminotetralin;
e) reduction of the carbamate to give 5,6-dialkoxy-2-methylaminotetralin.

The single steps are described in detail in the following:
1st step

The step consists in the condensation of 4-(2,3-dialkoxyphenyl)-2-oxo-3-butenoic acid with a suitable alkyl carbamate, for example methyl carbamate, carried out in an anhydrous organic solvent in the presence of a catalyst, for example p-toluenesulfonic acid, thus introducing the substituted amino group in a single step. The reaction takes place in nearly quantitative yields.

2nd step

The step consists in the catalytic hydrogenation of 3-alkyloxycarbonylamino-5-(2,3-dialkoxyphenyl)-2,5-dihydrofuran-2-one, using as catalyst for example palladium on carbon in alcoholic medium, thus obtaining 2-alkyloxycarbonylamino-4-(2,3-dialkoxyphenyl)butyric acid. The reaction takes place in nearly quantitative yields.

A further advantage can derive from that the reduction reaction of the dehydroamino acid 3-alkyloxycarbonylamino-5-(2,3-dialkoxyphenyl)-2,5-dihydrofuran-2-one can be carried out under enantioselectivity conditions to obtain 2-alkyloxycarbonylamino-4-(2,3-dialkoxyphenyl)butyric acid in an optically active form. For example, by asymmetric hydrogenation, particularly using suitable transition metal complexes with optically active ligands as catalyst, as described by R. M. Williams in Synthesis of Optically Active α-Amino Acids, 230–256, Pergamon Press and references cited.

3rd step

The step consists in the cyclization of 2-alkyloxycarbonylamino-4-(2,3-dialkoxyphenyl)butyric acid to give 2-alkyloxycarbonylamino-5,6-dialkoxy-1-tetralone. The intramolecular acylation reaction is carried out with conventional procedures, for example using polyphosphoric acid without solvent, by heating, still as an example, $PC_{15}$ and tin tetrachloride or other Friedel Crafts catalysts in a suitable solvent, for example methylene chloride, at room temperature (this second procedure is preferred in case of cyclization of an optically active product to obtain the tetralone corresponding enantiomer).

This step also takes place in nearly quantitative yields.
4th step

The reduction is carried out with conventional procedures, also on the optically active compound, for example by catalytic hydrogenation (see also the above methods). Yields are nearly quantitative.

5th step

It consists in the reduction of the alkyl carbamate group, in particular of the methoxycarbonylamino group, to methylamino group using a suitable reducing agent, in particular lithium aluminium hydride in a suitable solvent (for example tetrahydrofuran), in stoichiometric amounts. This process gives good yields (60–70%) and can also be applied to the optically active compound to obtain the corresponding enantiomer of 5,6-dialkoxy-2-alkylaminotetralin.

6th step

It consists in the deprotection of the catechol group with conventional (and enantiospecific) procedures, for example with concentrated hydrobromic acid and heating, to obtain 5,6-dihydroxy-2-methylaminotetralin in nearly quantitative yields.

The procedure is less manageable and longer than the preceding ones, but it gives very high overall yields and can also be applied to obtain optically active compounds.

A fourth procedure is carried out in four steps, starting from 4-(2,3-dimethoxyphenyl)-2-oxo-3-butenoic acid, and is applicable to obtain 5,6-dihydroxy-2-aminotetralin. This fourth process was subdivided into two parallel paths (A and B) which are nearly equivalent.

According to the paths A, compounds of formula (I) are prepared according to the following scheme 4:

Scheme 4

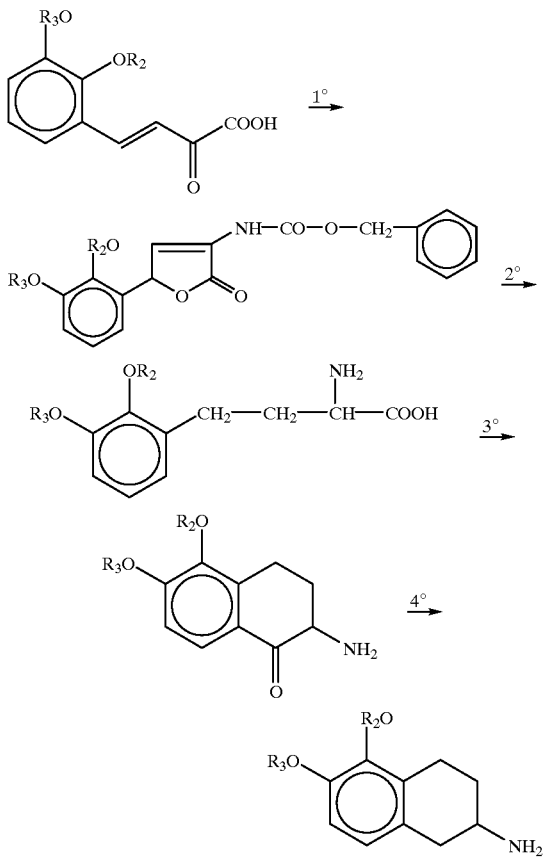

The steps are the following ones:
a) condensation of 4-(2,3-dialkoxyphenyl)-2-oxo-3-butenoic acid with benzyl carbamate to give 3-benzyloxycarbonylamino-5-(2,3-dialkoxyphenyl)-2,5-dihydrofuran-2-one;
b) catalytic reduction and simultaneous deprotection of 3-benzyloxycarbonylamino-5-(2,3-dialkoxyphenyl)-2,5-dihydrofuran-2-one to give 2-amino-4-(2,3-dialkoxyphenyl)butyric acid;
c) cyclization and simultaneous deprotection with HBr to give 5,6-dihydroxy-2-amino-1-tetralone;
d) reduction of 2-amino-5,6-dihydroxy-1-tetralone to give 2-amino-5,6-dihydroxytetralin.

The single steps are described in detail in the following:

1st step

The step consists in the condensation of 4-(2,3-dimethoxyphenyl)-2-oxo-3-butenoic acid with benzyl carbamate. The reaction is carried out in an anhydrous organic solvent in the presence of a catalyst, for example p-toluenesulfonic acid, thus introducing in a single step the protected amino group. The reaction takes place in nearly quantitative yields.

2nd step

The step consists in the catalytic hydrogenation of 3-benzyloxycarbonylamino-5-(2,3-dimethoxyphenyl)-2,5-dihydrofuran-2-one, for example with palladium on carbon as catalyst in alcoholic medium, thus obtaining directly in a single step the deprotected 2-amino-4-(2,3-dimethoxyphenyl)butyric acid. The reaction takes place in nearly quantitative yields. The reaction, as already discussed in the above process, can be carried out under enantioselectivity conditions, to obtain 2-amino-4-(2,3-dimethoxyphenyl)butyric acid in an optically active form.

3rd step

The step consists in the cyclization by intramolecular acylation of the amino acid with simultaneous deprotection of the catechol hydroxyls to give 5,6-dihydroxy-2-amino-1-tetralone. The reaction takes place, for example, using a suitable halohydric acid, for example 48% hydrobromic acid with heating. Yields are high (about 80%).

4th step

It consists in the reduction of 2-amino-5,6-dihydroxy-1-tetralone to give 2-amino-5,6-dihydroxytetralin by catalytic hydrogenation, for example using palladium on carbon as catalyst, in alcoholic or hydroalcoholic medium. Yields are nearly quantitative.

Alternatively, according to the paths B, in the 1st step, 4-(2,3-dimethoxyphenyl)-2-oxo-3-butenoic acid is condensed with an alkyl carbamate, for example methyl carbamate, under the same conditions.

The 2nd step consists in the catalytic hydrogenation of 3-alkyloxycarbonylamino-5-(2,3-dimethoxyphenyl)-2,5-dihydrofuran-2-one under the conditions described for the 2nd step of the Process 3.

The 3rd step consists in the cyclization by intramolecular acylation of the amino acid, with simultaneous deprotection of both the catechol hydroxyls and the amino group to give 5,6-dihydroxy-2-amino-1-tetralone.

The 4th step is carried out as described for the scheme 4 above.

This process, even though limited to the attainment of 2-amino-5,6-dihydroxytetralin, is particularly interesting industrially for the high yields, the easy operations and the low costs of the reagents.

It should be evidenced that, as it is known in literature, the catechol group is particularly unstable especially in basic medium, thus requiring the use of protecting groups or the salification. This involves problems difficult to solve, for example when organic salts of the product are desired.

The following examples further illustrate the invention.

EXAMPLE 1

2-Keto-4-(2,3-dimethoxyphenyl)-3-butenoic acid 300 ml of deionized water and 50 g of potassium hydroxide are placed into a 3 l flask. The mixture is stirred until dissolution, then 150 ml of ethanol and 100 g of 2,3-dimethoxybenzaldehyde are added. After that, 60.0 g of pyruvic acid are dropped therein (in about 30 minutes) and the mixture is stirred for about 15 minutes at a temperature from 35 to 40° C., then it is poured into 6500 ml of water and brought to markedly acid pH with about 140 ml of concentrated HCl. The mixture is cooled with stirring for about 30 minutes, then filtered washing with water and dried under vacuum at 60° C. to obtain an orange solid. Yield: 115 g, 81% (moles), 115% (weight);

TLC: methylene chloride/methanol/acetic acid 80/20/2;
Rf=0.5;
M.P.: 136–138° C.

EXAMPLE 2

2-Methylamino-4-(2,3-dimethoxyphenyl)butyric acid hydrochloride 70.0 g of 2-keto-4-(2,3-dimethoxyphenyl)-3-butenoic acid (0.30 moles) dissolved in 700 ml of ethanol are placed into a hydrogenator, then 43.0 g of an 8.03 M (0.34 mole) methylamine solution and glacial acetic acid under nitrogen atmosphere are added to pH from 8 to 9, keeping the temperature below 25° C. Stirring is continued for about 15 minutes, then 14.0 g of 5% Pd/C (about 50% humidity) are added, under hydrogen pressure (40 psi, room temperature) for 6 hours. The reaction mixture is then adjusted to markedly acid pH with concentrated HCl, filtered and the solution is evaporated to dryness. The resulting solid is taken up and triturated with heating (50° C.) with 300 ml of acetone, then it is left to cool under stirring, filtered and dried under vacuum at 40° C.

Yield: 51 g, 60% (moles), 73% (weight);

TLC: methylene chloride/methanol/acetic acid 75/20/10; Rf=0.5; Developer: ninhydrin. M.p.=165–166° C.

EXAMPLE 3

4-(2,3-Dimethoxyphenyl)-2-(N-methyl-N-benzyloxycarbonylamino)butyric acid 14.0 g of 2-methylamino-4-(2,3-dimethoxyphenyl) butyric acid hydrochloride (0.048 mole) and 24 ml of 4N NaOH are placed into a 250 ml flask, the resulting solution is cooled to about 0° C., then 9.1 g of benzyl chloroformate (0.053 mole) and 13.5 ml of 4N NaOH are dropped therein, at the same time but separately, to keep the ambient always slightly basic, cooling to a T<20° C., then keeping room temperature for about 2 hours. The reaction mixture is diluted with methanol HCl, washed with 100 ml of ethyl ether (2×50 ml) then acidified markedly with about 30 ml of 2N HCl and extracted with 150 ml of ethyl acetate (3×50 ml). The organic phase is dried over sodium sulphate, filtered and evaporated to dryness (40° C.) to obtain a clear, thick yellow oil, which is used directly for the subsequent step.

Yield: 18.5 g, about 100% (moles), about 132% (weight);

TLC: methylene chloride/methanol 90/10<; Rf=0.88. The protection of the amino group was obtained also with ethyl chloroformate with the same procedure and analogue results.

EXAMPLE 4

4-[2-(2,3-Dimethoxyphenyl)-ethyl]-N-methyl-2,5-oxazolidinedione 18.5 g of 4-(2,3-dimethoxyphenyl)-2-(N-methyl-N-benzyloxycarbonyl-amino)-butyric acid (0.048 mole) and 28.7 g of thionyl chloride are placed into a 250 ml round-bottomed flask, refluxing for 2 hours then distilling off under vacuum the thionyl chloride until obtaining a thick oil. The oil is taken up into 100 ml of hexane, stirring until solidification, then it is decanted and triturated with 100 ml more of hexane, filtered and dried under vacuum at 30° C. to obtain a fine crystalline powder. Yield: 12.5 g, 93% (moles), 68% (weight).

EXAMPLE 5

5,6-Dimethoxy-2-methylamino-1-tetralone hydrochloride 12.5 g of anhydrous aluminium chloride (0.094 mole) in 200 ml of methylene chloride are placed into a 3 l round-bottomed flask, under nitrogen atmosphere, cooling to 0° C., then 12.5 g of 4-[2-(2,3-Dimethoxyphenyl)-ethyl]-N-methyl-2,5-oxazolidindione dissolved in 200 ml of methylene chloride are added in about 10 minutes, keeping T<10° C. The mixture is stirred for 30 minutes at T<10° C., then for 1 hour a room temperature. The mixture is cooled again at 0° C. and 200 ml of water are dropped therein, keeping T<20° C., then the mixture is stirred at room temperature for about 1 hour and the organic phase is separated and extracted with water (3×400 ml). The combined aqueous phases are slowly alkalinized with 400 ml of a 20% $KHCO_3$ solution and extracted with 3×400 ml of chloroform. The organic phase is then dried over sodium sulphate, filtered, markedly acidified with methanolic HCl (1M) and evaporated to dryness to obtain a waxy compound, which is taken up into 150 ml of acetone a 50° C., stirred for one hour under stirring and left to stand overnight, then is filtered and dried under vacuum at room temperature. Yield: 8.2 g, 67% (moles);

TLC: methylene chloride/methanol, 90/10;
Rf=0.35; M.p.=208–209° C.

EXAMPLE 6

5,6-Dimethoxy-2-methylaminotetralin hydrochloride 14.0 g of 5,6-dimethoxy-2-methylamino-1-tetralone hydrochloride (0.051 mole), 400 ml of absolute ethanol, 10 ml of 1M methanolic HCl and 4.0 g of 5% Pd/C are placed into an autoclave (50% humidity), then the mixture is hydrogenated (P about 7 atm., T=80° C.) with stirring for 24 hours. The mixture is filtered, washing thoroughly the filtration cake with hot methanol, then the alcoholic solution is evaporated to dryness. The resulting solid is taken up into 150 ml of acetone, then the precipitate is filtered and dried under vacuum at 60° C. Yield: 10.8 g, 82% (moles), 77% (weight); M.p.=219–220° C.

EXAMPLE 7

5,6-Dihydroxy-2-methylaminotetralin HCl 41.4 g of dry $AlCl_3$ (310.4 moles), 230 ml of toluene and 20.0 g of 5,6-dimethoxy-2-methylaminotetralin HCl (77.6 moles) are placed into a 4-necked round-bottomed flask, with stirring, under a slight stream of dry nitrogen. Temperature is brought to 80° C. to obtain a stirrable brown mixture, is left at 80° C. for 4 hours, then cooled to room temperature and poured into ice-water (about 1000 ml total). The aqueous phase is separated and evaporated under vacuum (T about 80° C.). The whitish solid is triturated at room temperature in 750 ml of absolute ethanol, then dried at 60° C.

EXAMPLE 8

5,6-Dihydroxy-2-methylamino-1-tetralone bromidrato

A mixture of 15.0 g of acid 2-methylamino-4-(2,3-dimethoxyphenyl)-butyric acid hydrochloride (52 mmoles) and 100.0 ml of 48% aqueous HBr (900 mmoles) is refluxed, with stirring, for 3 hours, then is cooled to 0° C., the resulting precipitate is recovered by filtration, washed with acetone (50 ml) and dried under vacuum at 60° C. Yield: 13.5 g;

TLC: $CH_2Cl_2/CH_3OH/CH_3COOH$ 70/20/10 ($FeCl_2/K_3Fe(CN)_6$);

M.P.: 240–243° C.

EXAMPLE 9

5,6-Dihydroxy-2-methylaminotetralin hydrochloride

A mixture of 10.0 g of 5,6-dihydroxy- 2-methylamino-1-tetralone hydrobromide, 2.0 g of Pd/C 5%, 90 ml of water and 10 ml of 37% HCl is hydrogenated in an autoclave (Hastelloy) (20 atm, 80° C.) for 8–9 hours, then is filtered washing with hot water. The aqueous solution is concentrated under vacuum and the resulting solid is warm triturated with 100 ml of 37% hydrochloric acid, then cooled to 0° C. and filtered. The resulting solid is recrystallized from acetone and dried under vacuum at 60° C. Yield: 7.4 g.

EXAMPLE 10

3-Methoxycarbonylamino-5-(2,3-dimethoxyphenyl)-2,5-dihydrofuran-2-one 300 g of 2-keto-4-(2,3-dimethoxyphenyl)-3-butenoic acid, 2680 ml of toluene, 13.4 g of p-toluenesulfonic acid and 133.8 g of methyl carbamate are placed into a 6 l 4-necked round-bottomed flask in an oil-bath, the mixture is heated to 105° C. for 4 hours with stirring, and the present water is removed azeotropically, the mixture is filtered and the solution is evaporated to dryness under vacuum, then the residue is triturated for about 2 hours with 1260 ml of $Et_2O$, filtered washing with petroleum ether (40–70° C.) and dried under vacuum at 60° C. 313.00 g are obtained. (Yield 94%).

EXAMPLE 11

2-Methoxycarbonylamino-4-(2,3-dimethoxyphenyl) butyric acid 150 g of 3-methoxycarbonylamino-5(2,3-dimethoxyphenyl)-2,5-dihydro-furan-2-one and 1190 ml of $CH_3OH$ are placed into 2000 ml flasks of a Parr hydrogenator, then they are heated until complete dissolution with stirring (T about 64° C.); 30 g of 5% Pd/C are added and hydrogenation is started at 35 psi until $H_2$ is no longer absorbed (about 60 minutes). The disappearance of the starting compound is checked by TLC, then the mixture is filtered through Celite and the filtrate is evaporated to dryness, the resulting oil is precipitated with stirring by adding ethyl ether and petroleum ether, stirring is continued for about 30 minutes, then the mixture is filtered and dried under vacuum at 60° C. 141.6 g are obtained. (Yield 93%).

EXAMPLE 12

2-Methoxycarbonylamino-5,6-dimethoxy-1-tetralone 610 g of polyphosphoric acid are placed into a 5000 ml reactor, heating to 60° C., then 61 g of 2-methoxycarbonylamino-4-(2,3-dimethoxyphenyl)-butyric acid are added, with strong mechanical stirring. After about 20 min. stirring the mixture is diluted with water (2000 ml), then stirring is continued for 60 min. at room temperature. The resulting mixture is filtered and the solid is dissolved in 3000 ml of chloroform. The resulting solution is washed with water to neutral pH of the washings.

The organic phase is dried over sodium sulphate, filtered and evaporated to dryness under vacuum. The light brown solid residue is triturated for about 2 hours in 300 ml of ethyl ether and 50 ml of petroleum ether, then it is filtered and dried at 60° C. under vacuum, to obtain a powdery yellow-brown solid. Yield 51.2 g, 89.5% (moles), 84.0% (weight); T.L.C. Methylene chloride 95-Methanol 5; Rf=0.95.

EXAMPLE 13

2-Methoxycarbonylamino-5,6-dimethoxy- 1,2,3,4-tetrahydronaphthalene 50 g of 2-methoxycarbonylamino-5,6-dimethoxy-1-tetralone are dissolved in 500 ml of methanol in a 1000 ml flask, with stirring, 20 g of 5% Pd/C are added, then the whole is placed into an autoclave (Hastelloy) under hydrogen atmosphere at 80° C. and a pressure of 25 atm. for about 6 hours with stirring, after that the mixture is left to cool to about 30° C. in autoclave. The mixture is filtered through Celite and the filtrate is evaporated to dryness under vacuum. The resulting white solid is triturated in 400 ml of n-hexane at 60° C., then is left to cool to about 30° C. with stirring, filtered and dried under vacuum at 60° C., to obtain a whitish solid. Yield: 40.6 g, 85.5% (moles), 81.2% (weight); T.L.C. Methylene chloride 95-Methanol 5; Rf=0.76; M.p.=108.7–111.4° C.

EXAMPLE 14

5,6-Dimethoxy-2-methylamino-1,2,3,4-tetrahydronaphthalene hydrochloride 13.5 g of lithium aluminium hydride and 250 ml of anhydrous tetrahydrofuran are placed into a 1000 ml round-bottomed flask stirring for 15 min., then 80 g of 2-methoxycarbonylamino-5,6-dimethoxy-1,2,3,4-tetrahydronaphthalene dissolved in 350 ml anhydrous tetrahydrofuran are slowly dropped to keep temperature at about 60° C. Stirring is continued for about 30 min. and the mixture is filtered. The filtrate is cooled to about 0° C., water (1000 ml) is added with stirring, keeping the temperature at about 30° C. The reaction mixture is filtered and extracted with chloroform, the organic phase is dried over sodium sulphate, filtered organic phase is dried over sodium sulphate, filtered and acidified with methanol HCl. The solution is stirred for about 30 min., then evaporated to dryness. The resulting residue is triturated at 60° C. in 350 ml of acetonitrile, cooled to about 4° C. with stirring, then filtered and dried under vacuum at 50° C. to obtain a white solid. Yield 40.7 g, 52.4% (moles), 50.9% (weight).

EXAMPLE 15

5,6-Dihydroxy-2-methylamino-1,2,3,4-tetrahydronaphtalene hydrochloride

A suspension of 2-methylamino-5,6-dihydroxytetralin hydrochloride (5 g) in water (45 ml) is added to a solution of potassium carbonate (2.5 g) in water (25 ml) saturated with sodium sulphate. The mixture is stirred for some minutes, the formed solid is filtered washing with some water and acetone, then dried under vacuum at room temperature to obtain 3.8 g of a product.

¹H-NMR (DMSO-d6): 1.40 ppm (m, 1H, H3ax), 1.95 (m, 1H, H3eq), 2.40 (s, 3H, N-Me), 2.3–3.0 (m, 5H, H4, H2, H1), 5.0–6.0 (br, 2H, Or-H), 6.45 (d, 1H, H7), 6.56 (d, 1H, H8).

EI/MS (70 eV): m/and 193 (M⁺).

EXAMPLE 16 a) (−)-2-Methoxycarbonylamino-4-(2,3-dimethoxyphenyl)-butyric acid

A solution of 3-methoxycarbonylamino-5-(2,3-dimethoxyphenyl)-2,5-dihydrofuran-2-one (500 mg, 1.7 mmoles) in oxygen free methanol (0.25M) is placed into a Parr hydrogenator, the catalyst (SS)-EtDiPhos(COD)OTs (1.5 μmoles) is added and the mixture is stirred for 1.5 hr at room temperature under hydrogen pressure (30 psi).

The mixture is filtered and the filtrate is evaporated under vacuum, to obtain about 500 mg of the product (% e.e. (NMR)=95).

The product is further purified by crystallization.

NMR analysis (300 MHz, CDCl₃, in the presence of R(+)-α-methoxy-α-trifluoromethylphenylacetic acid, the signals at 3,842 ppm ((−) enantiomer) and 3,838 ppm ((+) enantiomer) were analyzed.

b) (+)-2-Methoxycarbonylamino-4-(2,3-dimethoxyphenyl)-butyric acid

A solution of 3-methoxycarbonylamino-5-(2,3-dimethoxyphenyl)-2,5-dihydrofuran-2-one (500 mg, 1.7 mmoles) in oxygen free methanol (0.25M) is placed into a Parr hydrogenator, the catalyst (RR)-EtDiPhos(COD)OTs (1.5 μmoles) is added and the mixture is stirred for 1.5 hr at room temperature under hydrogen pressure (30 psi).

The mixture is filtered and the filtrate is evaporated under vacuum, to obtain about 500 mg of the product (% e.e. (NMR)=92).

The product is further purified by crystallization.

NMR analysis (300 MHz, CDCl₃, in the presence of R(+)-α-methoxy-α-trifluoromethylphenylacetic acid, the signals at 3,842 ppm ((−) enantiomer) and 3,838 ppm ((+) enantiomer) were analyzed.

EXAMPLE 17

(+)-2-amino-4-(2,3-dimethoxyphenyl)-butyric acid

A solution of 3-benzyloxycarbonylamino-5-(2,3-dimethoxyphenyl)-2,5-dihydrofuran-2-one (500 mg, 1.35 mmoles) in oxygen free methanol (0.25M) is placed into a Parr hydrogenator, the catalyst (RR)-EtDiPhos(COD)OTs (1.3 μmoles) is added and the mixture is stirred for 3 hr at room temperature under hydrogen pressure (30 psi).

The mixture is filtered and the filtrate is evaporated under vacuum, to obtain 320 mg of the product (% e.e. (NMR)= 75).

The product is further purified by crystallization.

NMR analysis: signals at 3.34 ppm ((−) enantiomer) and 3.22 ppm ((+) enantiomer) were analyzed.

We claim:

1. A process for preparing 5,6-dihydroxy-2-amino-1,2,3,4-tetrahydronaphthalene of the formula (I):

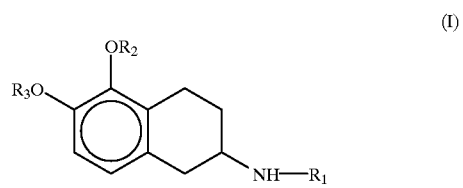

or an acid addition salt thereof, wherein:
   $R_1$, $R_2$ and $R_3$, which are each the same or different, are hydrogen or lower alkyl;
   which process comprises:
   a) condensing 2,3-dialkoxybenzaldehyde with pyruvic acid in an aqueous/alcoholic system in the presence of an inorganic base, to obtain 2-keto-4-(2,3-dialkoxyphenyl)butenoic acid;
   b) transforming the ketone at the 2-position into an amino or alkylamino group with simultaneous reduction of the double bond, to give, respectively, 2-amino or 2-alkylamino-4-(2,3-dialkoxyphenyl)butyric acid;
   c) transforming 2-amino- or 2-alkylamino-4-(2,3-dialkoxyphenyl)butyric acid into 4-[2-(2,3-dialkoxyphenyl)ethyl]-N-alkyl-2,5-oxazolidindione;
   d) intramolecularly cyclizing N-carboxyanhydride to give 5,6-dialkoxy-2-amino or 2-alkylamino-1-tetralone;
   e) reducing the ketone to give salified 5,6-dialkoxy-2-amino or 2-alkylamino-1,2,3,4-tetrahydronaphthalene and, optionally;
   f) effecting O-dealkylation to give salified, 5,6-dihydroxy-2-amino or 2-alkylamino-1,2,3,4-tetrahydronaphthalene, and, optionally; and
   g) transforming the resulting salt into the free base, or into another acid addition salt.

2. The process of claim 1, wherein in step a) a water/ethanol system is used and the inorganic base is potassium hydroxide.

3. The process of claim 1, wherein in step c), 4-(2,3-dialkoxyphenyl)-2-alkylamino butyric acid is first reacted with a chloroformate, to give the corresponding 2-N-alkyl-N-alkoxy-carbonylamino compound, which is subsequently cyclized to the corresponding cyclic N-carboxy anhydride.

4. The process of claim 1, wherein $R_1$ is methyl.

* * * * *